(12) United States Patent
Chang et al.

(10) Patent No.: US 7,045,121 B2
(45) Date of Patent: May 16, 2006

(54) OPHTHALMIC COMPOSITIONS FOR LUBRICATING EYES AND METHODS FOR MAKING AND USING SAME

(75) Inventors: James N. Chang, Newport Beach, CA (US); Teresa H. Kuan, Placentia, CA (US)

(73) Assignee: Allergan, Inc., Irvine, CA (US)

( * ) Notice: Subject to any disclaimer, the term of this patent is extended or adjusted under 35 U.S.C. 154(b) by 26 days.

(21) Appl. No.: 10/017,817

(22) Filed: Dec. 14, 2001

(65) Prior Publication Data

US 2004/0005289 A1    Jan. 8, 2004

(51) Int. Cl.
*A61K 31/47*   (2006.01)

(52) U.S. Cl. .................. 424/78.04; 514/57; 514/912

(58) Field of Classification Search ................ 514/57, 514/912; 424/78.04
See application file for complete search history.

(56) References Cited

U.S. PATENT DOCUMENTS

| | | | |
|---|---|---|---|
| 5,106,615 A | | 4/1992 | Dikstein |
| 5,212,162 A | | 5/1993 | Missel et al. |
| 5,460,834 A | * | 10/1995 | Bhagat ..................... 424/682 |
| 5,648,074 A | | 7/1997 | Park et al. |
| 5,858,346 A | | 1/1999 | Vehige et al. |

FOREIGN PATENT DOCUMENTS

| | | |
|---|---|---|
| EP | 0590786 | 4/1994 |
| WO | WO 0101959 | 1/2001 |

OTHER PUBLICATIONS

Aqualon® CMC, Physical and Chemical Properties, Hercules Incorporated, 1999.
Abstract Submitted to ARVO for Conference held Nov. 30, 2001: The Effect of Different CMC Materials in Artificial Tears in the Tear Layer on Contrast Sensitivity.
LaMotte et al. "The effect of artificial tears with different CMC formulations on contrast sensitivity", ARVO Annual meeting abstract search and program planner, vol. 2002, 2002 pg abstract No. 3151.
Allergan "Refresh lubricant eyedrops" retrieved on Apr. 3, 2003 from: www.drugstore.com/qxp72838_333181_seaspider/allergan/refresh_liquigel_lubricant_eye_drops.htm.
Simmons P A, "Refresh Liquigel (TM): A new approach to the treatment of persistent dry eye", Practical Optometry 2002 Canada, vol. 13, No. 2, 2002, pp. 68-71.

* cited by examiner

*Primary Examiner*—Zohreh Fay
(74) *Attorney, Agent, or Firm*—Stout, Uxa, Buyan & Mullins, LLP; Frank J. Uxa; Carlos A. Fisher

(57) ABSTRACT

Ophthalmic compositions include an ophthalmically acceptable carrier component, for example, an aqueous-based carrier, and a plurality of polyanionic component portions having different molecular weights. In one embodiment, the polyanionic component includes a first polyanionic component portion having a first molecular weight; and a second polyanionic component portion having a different second molecular weight. Each of the first and second polyanionic component portions is present in an amount effective to provide lubrication to an eye when the composition is administered to an eye. Methods of making and using such compositions are also disclosed.

23 Claims, No Drawings

OPHTHALMIC COMPOSITIONS FOR LUBRICATING EYES AND METHODS FOR MAKING AND USING SAME

BACKGROUND OF THE INVENTION

The present invention relates to ophthalmic compositions useful for lubricating eyes to which such compositions are administered. More particularly, the present invention relates to compositions including mixtures of components which are very effective in providing desired eye lubrication without unduly interfering with vision, to methods for making ophthalmic compositions and to methods for lubricating eyes and treating eyes having dry eye syndrome using ophthalmic compositions.

Mammalian eyes, such as human eyes, advantageously are adequately lubricated to provide eye comfort and to more effectively provide good, clear vision, ordinarily, such lubrication is obtained naturally from a tear film, which is formed over the outer, exposed surface of the eye. However, in many instances, this tear film is not present in a sufficient amount to effectively lubricate the eye. A condition known as "dry eye" can result from inadequate lubrication of the eye.

A relatively large number of compositions have been suggested for use in providing eye lubrication. For example, artificial tears, that is materials having chemical compositions which mimic or resemble natural tears, have been used. Such artificial tears often require very frequent use since they are rapidly lost from the eye. In addition, although they wet the eye, their value in lubricating the eye is somewhat less than optimal. Compositions which include specific lubricants have been suggested. For example, a number of materials including carboxy methylcelluloses (CMCs) have been used in eyes. These compositions, which are generally effective, have certain shortcomings. For example, certain low viscosity CMC-containing materials require frequent administration since they are rapidly lost from the eye. In other words, such materials do not adhere to the eye sufficiently to provide effective lubrication without frequent replenishment. High viscosity CMC-containing materials effectively adhere to eyes but are disadvantageously disruptive to clear vision for relatively long periods of time after administration.

There continues to be a need for compositions which are effective to provide lubrication to eyes that can be conveniently used, e.g., administered over acceptable intervals of time, rather than very frequently, and without being unduly disruptive to clear vision.

SUMMARY OF THE INVENTION

New ophthalmic compositions for providing lubrication to eyes, and methods for making and using same, have been discovered. The present compositions very effectively lubricate eyes, for example, eyes suffering from "dry eye" syndrome. These compositions are relatively straightforward, can be easily and cost effectively manufactured and can be used much like prior art eye lubricating materials. Importantly, the present compositions include combinations of materials which preferably provide relatively long lasting effective eye lubrication, for example, without the need for very frequent readministration or replenishment to the eye, and which are advantageously not unduly disruptive to clear vision from the eye being treated.

In one broad aspect, the present invention is directed to ophthalmic compositions comprising an ophthalmically acceptable carrier component and a polyanionic component including at least two polyanionic component portions. Each polyanionic component portion has a different molecular weight. In one very useful embodiment, the polyanionic component includes a first polyanionic component portion having a first molecular weight; and a second polyanionic component having a second molecular weight. Advantageously each of the polyanionic component portions is present in an amount effective to provide lubrication to an eye when the composition is administered to the eye. Preferably, each of the polyanionic component portions is present in an amount of at least about 0.1% w/v of the composition.

As noted above, each of the polyanionic component portions has a different average molecular weight. In one embodiment, the first polyanionic component portion has a first average molecular weight which is greater than the second average molecular weight of the second polyanionic component portion. The difference in average molecular weight between the polyanionic component portions, for example, between the first and second polyanionic component portions, preferably is at least about 10,000 and more preferably is at least about 50,000.

As used herein the term "molecular weight" refers to weight average molecular weight, as that term is commonly known within the polymer art, and can be measured or determined using procedures and/or techniques well known in this art.

Any suitable polyanionic component may be employed in accordance with the present invention. Such polyanionic component should be ophthalmically acceptable, compatible with the other components of the composition, and effective, in ophthalmically reasonable concentrations, to provide lubrication to the eye when administered to the eye and to otherwise function in accordance with the present invention. In one useful embodiment, at least one, and preferably all of the polyanionic component portions are selected from anionic cellulosic derivatives and mixtures thereof. A very useful embodiment provides that at least one, and preferably all, of the polyanionic component portions be selected from the group consisting of carboxy methyl celluloses and mixtures thereof.

Other suitable polyanionic components may be employed. For example, at least one, and preferably all, of the polyanionic component portions may be selected from anionic homopolymers and copolymers comprising units of one or more of acrylic acid, methacrylic acid, metal acrylates and metal methacrylates, and mixtures thereof. A very useful polyanionic component from which at least one, and preferably all, of the first and second polyanionic component portions may be selected are homopolymers and copolymers comprising units of one or more of acrylic acid, metal acrylates and mixtures thereof.

The present compositions preferably are solutions, although other forms, such as ointments, gels, and the like, may be employed.

The carrier component is ophthalmically acceptable and may include one or more components which are effective in providing such ophthalmic acceptability and/or otherwise benefitting the composition and/or the eye to which the composition is administered and/or the patient whose eye is being treated. Advantageously, the carrier component is aqueous-based, for example, comprising a major amount that is at least about 50% by weight, of water.

The present compositions may be prepared using conventional procedures and techniques. For example, the present compositions can be prepared by blending the components together, such as in one bulk.

In another broad aspect of the present invention, methods for providing lubrication to eyes are provided. Such methods comprise administering an effective amount of a composition in accordance with the present invention to an eye in need of lubrication. In one very useful embodiment, the eye to which the composition is administered has dry eye syndrome or has a propensity toward dry eye syndrome. Preferably, the present administering step is repeated at least once, and more preferably as needed to effectively lubricate the eye to which the composition is administered.

Each and every feature described herein, and each and every combination of two or more of such features, is included within the scope of the present invention provided that the features included in such a combination are not mutually inconsistent.

These and other aspects and advantages of the present invention are apparent in the following detailed description, examples and claims.

DETAILED DESCRIPTION

The present invention involves ophthalmic compositions, which are advantageously ophthalmically acceptable, comprising an ophthalmically acceptable carrier component and a polyanionic component including at least two polyanionic component portions.

A composition, carrier component or other material is "ophthalmically acceptable" when it is compatible with ocular tissue, that is, it does not cause significant or undue detrimental effects when brought into contact with ocular tissue. Preferably, the ophthalmically acceptable material is also compatible with other components of the present compositions.

As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from the group consisting of polymeric materials having multiple anionic charges and mixtures thereof.

Each polyanionic component portion has a different molecular weight. In one very useful embodiment, the polyanionic component includes a first polyanionic component portion having a first molecular weight; and a second polyanionic component having a second molecular weight. Advantageously each of the polyanionic component portions is present in an amount effective to provide lubrication to an eye when the composition is administered to the eye. Preferably, each of the polyanionic component portions is present in an amount of at least about 0.1% w/v of the composition.

Preferably, the composition has an increased ability to adhere to an eye when the composition is administered to an eye relative to a substantially identical composition having an equal total amount of the polyanionic component and substantially no first polyanionic component portion. With regard to the increased ability to adhere to an eye feature noted above, the present composition preferably is effective to provide effective lubrication over a longer period of time before requiring readministration relative to a substantially identical composition having an equal total amount of the polyanionic component and substantially no first polyanionic component portion.

Advantageously, the composition has a reduced ability to cause blurriness of vision in an eye when the composition is administered to the eye relative to a substantially identical composition having an equal total amount of the polyanionic component and substantially no second polyanionic component portion. The reduced ability to cause blurriness of vision in an eye can be looked at as being a measure of the amount of time required, after the composition is administered to the eye, for the eye to regain clear vision, that is vision not blurred by the administration of the composition. In other words, the present composition, after being administered to the eye, preferably allows the eye to provide clear vision in a reduced amount of time relative to a substantially identical composition having an equal total amount of the polyanionic component and substantially no second polyanionic component portion.

In one embodiment, the at least two polyanionic component portions, for example, the first and second polyanionic component portions, other than having different molecular weights, have substantially similar chemical structures. However, the at least two polyanionic component portions may have different chemical structures. Each of the polyanionic component portions, for example, the first and second polyanionic component portions, preferably is separately derived. In other words, it is preferred that each of the polyanionic component portions be combined into the present compositions as separate materials.

Any suitable polyanionic component may be employed in accordance with the present invention provided that it functions as described herein and has no substantial detrimental effect on the composition as a whole or on the eye to which the composition is administered. The polyanionic component is preferably ophthalmically acceptable at the concentrations used. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the present compositions at ambient (room) temperature.

Examples of suitable polyanionic components useful in the present compositions include, without limitation, anionic cellulose derivatives, anionic acrylic acid-containing polymers, anionic methacrylic acid-containing polymers, anionic amino acid-containing polymers and mixtures thereof. Anionic cellulose derivatives are very useful in the present invention.

A particularly useful class of polyanionic components are one or more polymeric materials having multiple anionic charges. Examples include, but are not limited to:
    metal carboxy methylcelluloses
    metal carboxy methylhydroxyethylcelluloses
    metal carboxy methylstarchs
    metal carboxy methylhydroxyethylstarchs
    hydrolyzed polyacrylamides and polyacrylonitriles
    heparin
    gucoaminoglycans
    hyaluronic acid
    chondroitin sulfate
    dermatan sulfate
    peptides and polypeptides
    alginic acid
    metal alginates
    homopolymers and copolymers of one or more of:
        acrylic and methacrylic acids metal acrylates and methacrylates
vinylsulfonic acid
metal vinylsulfonate
amino acids, such as aspartic acid, glutamic acid and the like
metal salts of amino acids
p-styrenesulfonic acid
metal p-styrenesulfonate
2-methacryloyloxyethylsulfonic acids
metal 2-methacryloyloxyethylsulfonates
3-methacryloyloxy-2-hydroxypropylsulonic acids
metal 3-methacryloyloxy-2-hydroxypropylsulfonates
2-acrylamido-2-methylpropanesulfonic acids
metal 2-acrylamido-2-methylpropanesulfonates
allylsulfonic acid
metal allylsulfonate and the like.

Excellent results are achieved using polyanionic components selected from carboxy methylcelluloses and mixtures thereof, for example, alkali metal and/or alkaline earth metal carboxy methylcelluloses.

The present compositions preferably are solutions, although other forms, such as ointments gels, and the like, may be employed.

The carrier component is ophthalmically acceptable and may include one or more components which are effective in providing such ophthalmic acceptability and/or otherwise benefitting the composition and/or the eye to which the composition is administered and/or the patient whose eye is being treated. Advantageously, the carrier component is aqueous-based, for example, comprising a major amount that is at least about 50% by weight, of water. Other components which may be included in the carrier components include, without limitation, buffer components, tonicity components, preservative-components, pH adjustors, components commonly found in artificial tears, such as one or more electrolytes, and the like and mixtures thereof.

The present compositions preferably have viscosities in excess of the viscosity of water. In one embodiment, the viscosity of the present compositions is at least about 10 cps (centipoise), more preferably in a range of about 10 cps to about 500 cps or about 1,000 cps. Advantageously, the viscosity of the present composition is in a range of about 15 cps or about 30 cps or about 70 to about 150 cps or about 200 cps or about 300 cps or about 500 cps. The viscosity of the present composition may be measured in any suitable, for example, conventional manner. A conventional Brookfield viscometer measuring such viscosities.

As noted previously, each of the polyanionic component portions, that is, for example, at least the first and second polyanionic component portions, present in an amount of at least about 0.1% (w/v) of the composition. In one very useful embodiment, the polyanionic component is present in an amount in a range of about 0.2% to about 5%, preferably about 0.4% to about 2.5%, more preferably about 0.6% to about 1.8% and still more preferably about 0.8% to about 1.3% (w/v) of the composition.

The weight ratio of the first polyanionic component portion to the second polyanionic component portion may vary over a wide range. In one embodiment, the ratio weight of the first portion to the second portion is in the range of about 0.02 to about 50, preferably about 0.1 to about 10, and more preferably about 0.25 to about 4.

The different, for example, first and second, polyanionic component portions of the present compositions preferably are separately derived. Put another way, it is preferred that the different, e.g., first and second, polyanionic component portions be blended into the present compositions from different sources. The molecular weights of the different polyanionic component portions preferably differ by at least about 10,000, and more preferably at least about 50,000.

In a very useful embodiment, the polyanionic component further comprises a third polyanionic component portion having a third molecular weight which is different from the first and second molecular weights. The third polyanionic component portion preferably is present in an amount effective to provide lubrication to an eye when the composition is administered to an eye and/or at least about 0.1% (w/v) of the composition.

Other components which may be included in the carrier components include, without limitation, buffer components, tonicity components, preservative-components, pH adjustors, components commonly found in artificial tears, such as one or more electrolytes, and the like and mixtures thereof. In one very useful embodiment the carrier component includes at least one of the following: an effective amount of a buffer component; an effective amount of a tonicity component; an effective amount of a preservative component; and water.

These additional components preferably are ophthalmically acceptable and can be chosen from materials which are conventionally employed in ophthalmic compositions, for example, compositions used to treat eyes afflicted with dry eye syndrome, artificial tear formulations and the like.

Acceptable effective concentrations for these additional components in the compositions of the invention are readily apparent to the skilled practitioner.

The carrier component preferably includes an effective amount of a tonicity adjusting component to provide the composition with the desired tonicity. The carrier component preferably includes a buffer component which is present in an amount effective to maintain the pH of the composition in the desired range. Among the suitable tonicity adjusting components that may be employed are those conventionally used in ophthalmic compositions, such as one or more various inorganic salts and the like. Sodium chloride, potassium chloride, mannitol, dextrose, glycerin, propylene glycol and the like and mixtures thereof are very useful tonicity adjusting components. Among the suitable buffer components or buffering agents that may be employed are those conventionally used in ophthalmic compositions. The buffer salts include alkali metal, alkaline earth metal and/or ammonium salts. Conventional organic buffers, such as Goode's buffer and the like, may also be employed.

Any suitable preservative component may be included in the present compositions provided that such components is effective as a preservative in the presence of the polyanionic component. Thus, it is important that the preservative component be substantially unaffected by the presence of the polyanionic component. Of course, the preservative component chosen depends on various factors, for example, the specific polyanionic component present, the other components present in the composition, etc. Examples of the useful preservative components include, but are not limited to, per-salts, such as perborates, percarbonates and the like; peroxides, such as very low concentrations, e.g., about 50 to about 200 ppm (w/v), of hydrogen peroxide and the like; alcohols, such as benzyl alcohol, chlorbutanol and like; sorbic acid and ophthalmically acceptable salts thereof and mixtures thereof.

The amount of preservative component included in the present compositions containing such a component varies over a relatively wide range depending, for example, on the specific preservative component employed. The amount of such component preferably is in the range of about 0.000001% to about 0.05% or more (w/v) of the present composition.

One particularly useful class of preservative components are chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes, such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include that sold under the trademark Purite® by Bio-Cide International, Inc. that sold under the trademark Dura Klor by Rio Linda Chemical Company, Inc., and that sold under the trademark Anthium Dioxide by International Dioxide, Inc.

The chlorine dioxide precursor is included in the present compositions to effectively preserve the compositions. Such effective preserving concentrations preferably are in the range of about 0.0002 or about 0.002 to about 0.02% (w/v) of the present compositions.

In the event that chlorine dioxide precursors are employed as preservative components, the compositions preferably have an osmolality of at least about 200 mOsmol/kg and are buffered to maintain the pH within an acceptable physiological range, for example, a range of about 6 to about 8 or about 10.

The present compositions preferably include an effective amount of an electrolyte component, that is one or more electrolytes, for example, such as is found in natural tears and artificial tear formulations. Examples of particularly useful such electrolytes for inclusion in the present compositions include, without limitation, alkaline earth metal salts, such as alkaline earth metal inorganic salts, and mixtures thereof, e.g., calcium salts, magnesium salts and mixtures thereof. Very good results are obtained using an electrolyte component selected from calcium chloride, magnesium chloride and mixtures thereof.

The amount or concentration of such electrolyte component in the present compositions can vary widely and depends on various factors, for example, the specific electrolyte component being employed, the specific composition in which the electrolyte is to be included and the like factors. In one useful embodiment, the amount of the electrolyte component is chosen to at least partially resemble, or even substantially resemble, the electrolyte concentration in natural human tears. Preferably, the concentration of the electrolyte component is in the range of about 0.01 to about 0.5 or about 1% of the present composition.

The present compositions may be prepared using conventional procedures and techniques. For example, the present compositions can be prepared by blending the components together, such as in one bulk.

To illustrate, in one embodiment, the polyanionic component portions are combined with purified water and caused to disperse in the purified water, for example, by mixing and/or agitation. The other components, such as the buffer component, tonicity component, electrolyte component, preservative component and the like, are introduced as the mixing continues. The final mixture is sterilized, such as steam sterilized, for example, at temperatures of at least about 100° C., such as in a range of about 120° C. to about 130° C., for a time of at least about 15 minutes or at least about 30 minutes, such as in a range of about 45 to about 60 minutes. In one embodiment, the preservative component preferably is added to the mixture after sterilization. The final product preferably is filtered, for example, through a 20 micron sterilized cartridge filter, such as a 20 micron clarity filter cartridge, e.g., sold by Pall under the tradename HDC II, to provide a clear, smooth solution, which is then aseptically filled into containers, for example, low density polyethylene teal containers.

Alternately, each of the polyanionic component portions can be mixed with purified water to obtain individual polyanionic component portion solutions. By mixing the individual polyanionic component portion solutions together, a blend is easily and effectively obtained having the desired, controlled ratio of the individual polyanionic component portions. The blended solution can then be combined with the other components, sterilized and filled into containers, as noted above.

In one particularly useful embodiment, a solution of the polyanionic component portions and purified water is obtained, as noted above. This solution is then sterilized, for example, as noted above. Separately, the other components to be included in the final composition are solubilized in purified water. This latter solution is sterile filtered, for example, through a 0.2 micron sterilizing filter, such as that sold by Pall under the tradename Suporflow, into the polyanionic component-containing solution to form the final solution. The final solution is filtered, for example, as noted above, to provide a clear, smooth solution which is then aseptically filled into containers, as noted above.

The present compositions may be effectively used, as needed, by methods which comprise administering an effective amount of the composition to an eye in need of lubrication, for example, an eye afflicted with dry eye syndrome or having a propensity toward dry eye syndrome. The administering step may be repeated as needed to provide effective lubrication to such eye. The mode of administration of the present composition depends on the form of the composition. For example, if the composition is a solution, drops of the composition may be applied to the eye, e.g., from a conventional eye dropper. In general, the present compositions may be applied to the surface of the eye in substantially the same way as conventional ophthalmic compositions are applied. Such administration of the present compositions does provide substantial and unexpected benefits, as described elsewhere herein.

The following non-limiting examples illustrate certain aspects of the present invention.

EXAMPLE 1

An ophthalmic formulation in accordance with the present invention is prepared as follows:

A mixture of purified water, high molecular weight sodium carboxy methyl celluloses (HCMC) and medium molecular weight sodium carboxy methyl celluloses (MCMC) is produced by blending the components together with mixing. The HCMC has a weight average molecular weight of about 700,000, while the MCMC has a weight average molecular weight of about 250,000. Both the HCMC and the MCMC are commercially available and are sold by Hercules under the trademark AQUALON®

Various other materials are blended with this mixture to form a solution having the following composition:

| Ingredient | Concentration, % (w/v) |
|---|---|
| HCMC | 0.30 |
| MCMC | 0.70 |
| Sodium Chloride | 0.37 |
| Boric Acid | 0.60 |
| Sodium Borate Decahydrate | 0.045 |
| Potassium-chloride | 0.14 |
| Calcium Chloride Dihydrate | 0.006 |
| Magnesium Chloride Hexahydrate | 0.006 |
| Purite ®[1] | 0.0075 |
| Sodium Hydroxide 1N | Adjust pH to 7.2 |
| Hydrochloric Acid 1N | Adjust pH to 7.2 |
| Purified water | q.s. ad |

(1) Purite® is a registered trademark of Bio-Cide International, Inc. for stabilized chlorine dioxide. This material is added to the mixture after heat sterilization.

The viscosity of this solution, measured by a conventional Brookfield viscometer, is 136 cps.

The solution is then heat sterilized in a closed autoclave, at 123° C. for 45 minutes.

The viscosity of the sterilized solution measured by a conventional Brookfield viscometer, is 80 cps.

The sterilized solution, in the form of eye drops, is administered to the eyes of a human patient having dry eye syndrome. Such administration is effective to lubricate the patient's eyes and at least reduce the severity (for example, in terms of reducing the symptoms) of the dry eye syndrome. Moreover, such lubrication/symptom reduction advantageously lasts for a longer period of time (per administration) that is achieved by administering a substantially identical composition including the same total amount of sodium carboxy methylcellulose without the HCMC. In addition, the human patient regains clear vision (that is non-blurry vision) more rapidly after administration of the sterilized solution relative to the time required to regain clear vision after administration of a substantially identical composition including the same total amount of sodium carboxy methylcellulose without the MCMC.

In short, the sterilized solution, when administered to the eyes of the human patient, effectively provides relief from dry eye syndrome for relatively long periods of time (between administrations) with reduced interference with the patient's ability to see clearly.

EXAMPLES 2 TO 4

Example 1 is repeated three times except that different amounts of HCMC and MCMC are employed. The amounts of HCMC and MCMC in each of these formulations and the viscosities of each of these formulations are as follows:

|  | Example 2 | Example 3 | Example 4 |
|---|---|---|---|
| HCMC, % (w/v) | 0.45 | 0.35 | 0.25 |
| MCMC, % (w/v) | 0.55 | 0.65 | 0.75 |
| Viscosity |  |  |  |
| Before sterilization | (not measured) | (not measured) | 108 cps |
| After sterilization | 101 cps | 78 cps | 62 cps |

Each of these sterilized solutions is administered to the eyes of a human patient having dry eye syndrome. Each such administration is effective to lubricate the patient's eyes and to at least reduce the severity of the dry eye syndrome. As described in detail with regard to the formulation of Example 1, each of the sterilized solutions of Examples 2, 3 and 4, when administered to the eyes of a human patient, effectively provides relief from the dry eye condition for relatively long periods of time (between administrations) with reduced interference with the patient's ability to see clearly.

EXAMPLES 5 TO 10

Example 1 is repeated an additional six (6) times except that the MCMC is replaced by low molecular weight sodium carboxy methylcellulose (LCMC), and various different ratios of HCMC and LCMC are used. The weight average molecular weight of the LCMC is 90,000. The LCMC is commercially available and is sold by Hercules under the trademark AQUALON®.

The amounts of HCMC and LCMC in each of these formulations and the viscosities of each of these formulations are as follows:

|  | Example 5 | Example 6 | Example 7 | Example 8 | Example 9 | Example 10 |
|---|---|---|---|---|---|---|
| HCMC, % w/v | 0.80 | 0.70 | 0.60 | 0.50 | 0.45 | 0.40 |
| LCMC, % w/v | 0.20 | 0.30 | 0.40 | 0.50 | 0.55 | 0.60 |
| Viscosity |  |  |  |  |  |  |
| Before Sterilization | not measured | not measured | not measured | not measured | 102 cps | not measured |
| After Sterilization | 247.7 cps | 132 cps | 93.8 cps | 59.4 cps | 63 cps | 38.2 cps |

Each of these sterilized solutions, in the form of eye drops, is administered to the eyes of a human patient having dry eye syndrome. Each such administration is effective to lubricate the patient's eyes and at least reduce the severity (for example, in terms of reducing the symptoms) of the dry eye condition. Moreover, such lubrication/symptom reduction lasts advantageously for a longer period of time (per administration) that is achieved by administering a substantially identical composition including the same total amount of sodium carboxy methyl-cellulose without the HCMC. In addition, each of the human patients regain clear vision (that is non-blurry vision) more rapidly after administration of the sterilized solution relative to the time required to regain clear vision after administration of a substantially identical composition including the same total amount of sodium carboxy methylcellulose without the LCMC.

In short, the sterilized solutions of Examples 5 to 10, when administered to the eyes of the human patient, effectively provide relief from the dry eye condition for relatively long periods of time (between administrations) with reduced interference with the patient's ability to see clearly.

EXAMPLES 11 TO 14 (COMPARATIVE)

Example 1 is repeated four (4) further times except that only a single molecular weight sodium carboxy methylcellulose is used in each formulation.

The amount and type of sodium carboxy methylcellulose in each of these formulations and the viscosities of each of these formulations are as follows:

|  | Example 11 | Example 12 | Example 13 | Example 14 |
|---|---|---|---|---|
| HCMC, % (w/v) | 1.0 | 1.0 | — | — |
| MCMC, % (w/v) | — | — | 1.0 | — |
| LCMC, % (w/v) | — | — | — | 1.0 |
| Viscosity |  |  |  |  |
| Before sterilization | 1002 cps | 1002 cps | 40 cps | 6.1 cps |
| After sterilization | 407 cps | 442 cps | 34 cps | 5.2 cps |

These results indicate that heat sterilization has a significant effect on the viscosity of the formulations of Examples 11 and 12 which both include HCMC. Without wishing to limit the invention to any particular theory of operation, it is believed that the heat sterilization degrades the HCMC so that the weight average molecular weight of this material is somewhat reduced after such sterilization. However, it is important to note that even after such sterilization a clear and substantial distinction, for example, in terms of viscosity, exists between the HCMC-containing formulations (Example 11 and 12) and the MCMC-containing formulation (Example 13) and the LCMC-containing formulation (Example 14). In other words, even after heat sterilization, the HCMC-containing formulation includes effective amounts of carboxy methyl-cellulose with a substantially higher molecular weight than the carboxy methylcellulose present in the heat sterilized MCMC-containing and LCMC-containing formulations. The difference between the weight average molecular weight of the carboxy methylcellulose in the sterilized HCMC-containing composition and the sterilized MCMC-containing composition is believed to be (based on a correlation of viscosities before and after sterilization) at least about 75,000 or about 80,000. Similarly the difference between the weight average molecular weight of the carboxy methylcellulose in the sterilized MCMC-containing composition and the sterilized LCMC-containing composition is believed to be at least about 125,000.

While this invention has been described with respect to various specific examples and embodiments, it is to be understood that the invention is not limited thereto and that it can be variously practiced with the scope of the following claims.

What is claimed is:

1. An ophthalmic composition comprising:
   an ophthalmically acceptable carrier component; and
   a polyanionic component including a first polyanionic component portion having a first weight average molecular weight in a range of about 250,000 to about 700,000; and a second polyanionic component portion having a second weight average molecular weight in a range of about 90,000 to about 250,000; the first and second polyanionic component portions each being present in an amount effective to provide lubrication to an eye when the composition is administered to an eye, the first and second molecular weights being different by at least about 50,000, the first polyanionic component portion and the second polyanionic component portion being selected from the group consisting of anionic cellulosic derivatives and mixtures thereof.

2. The composition of claim 1 wherein the composition has an increased ability to adhere to an eye when the composition is administered to an eye relative to a substantially identical composition having an equal total amount of the polyanionic component and substantially no first polyanionic component portion.

3. The composition of claim 1 wherein the composition has a reduced ability to cause blurriness of vision in an eye when the composition is administered to an eye relative to a substantially identical composition having an equal total amount of the polyanionic component and substantially no second polyanionic component portion.

4. The composition of claim 2 wherein the composition has a reduced ability to cause blurriness of vision in an eye when the composition is administered to an eye relative to a substantially identical composition having an equal total amount of polyanionic component and substantially no second polyanionic component.

5. The composition of claim 1 wherein at least one of the first and second polyanionic component portions is selected from the group consisting of carboxy methyl celluloses and mixtures thereof.

6. The composition of claim 1 wherein each of the first and second polyanionic component portions is present in an amount of at least about 0.1% (w/v) of the composition.

7. The composition of claim 1 which has a viscosity in a range of about 15 cps to about 200 cps.

8. The composition of claim 1 wherein the polyanionic component is present in an amount in a range of about 0.2% to about 5% (w/v) of the composition.

9. The composition of claim 1 wherein the polyanionic component is present in an amount in a range of about 0.6% to about 1.8%.

10. The composition of claim 1 wherein the weight ratio of the first polyanionic component portion to the second polyanionic component portion is in a range of about 0.02 to about 50.

11. The composition of claim 1 wherein the weight ratio of the first polyanionic component portion to the second polyanionic component portion is in a range of about 0.25 to about 4.

12. The composition of claim 1 wherein the carrier component includes at least one of the following: an effective amount of a buffer component; an effective amount of a tonicity component; an effective amount of a preservative component; and water.

13. The composition of claim 1 where the first and second polyanionic component portions are separately derived.

14. An ophthalmic composition comprising:
    an ophthalmically acceptable carrier component; and a polyanionic component including at least a first polyanionic component portion having a weight average molecular weight in a range of about 250,000 to about 700,000 and a second polyanionic component portion having a weight average molecular weight in a range of about 90,000 to about 250,000, the first polyanionic component portion having a weight average molecular weight which differs from the weight average molecular weight of the second polyanionic component portion by at least about 50,000, and each of the first and second polyanionic component portions being present in an amount of at least about 0.1% w/v of the composition, the at least two polyanionic component portions being selected from the group consisting of anionic cellulosic derivatives and mixtures thereof.

15. The composition of claim 14 wherein the composition has an increased ability to adhere to an eye when the composition is administered to an eye relative to a substantially identical composition having an equal total amount of polyanionic component and substantially no polyanionic component portion with the greatest molecular weight.

16. The composition of claim 14 wherein the composition has a reduced ability to cause blurriness of vision in an eye when the composition is administered to an eye relative to a substantially identical composition having an equal total amount of polyanionic component and substantially no polyanionic component portion having the lowest molecular weight.

17. The composition of claim 14 wherein each of the polyanionic component portions, other than having different molecular weights, has a substantially similar chemical structure.

18. The composition of claim 14 wherein all the polyanionic component portions are selected from the group consisting of carboxyl methyl celluloses and mixtures thereof.

19. The composition of claim 14 wherein each of the polyanionic component portions is present in an amount of at least about 0.2% (w/v) of the composition.

20. The composition of claim 14 which has a viscosity in a range of about 15 cps to about 200 cps.

21. The composition of claim 14 wherein the polyanionic component is present in an amount in a range of about 0.2% to about 5% (w/v) of the composition.

22. The composition of claim 14 wherein the polyanionic component is present in an amount in a range of about 0.6% to about 1.8% (w/v) of the composition.

23. The composition of claim 14 wherein the carrier component includes at least one of the following: an effective amount of a buffer component; an effective amount of a tonicity component; an effective amount of a preservative component; and water.

* * * * *

UNITED STATES PATENT AND TRADEMARK OFFICE
CERTIFICATE OF CORRECTION

PATENT NO. : 7,045,121 B2  
APPLICATION NO. : 10/017817  
DATED : May 16, 2006  
INVENTOR(S) : Chang et al.

It is certified that error appears in the above-identified patent and that said Letters Patent is hereby corrected as shown below:

Column 1

Line 18, delete the comma after "vision" and insert a period in place thereof.

Line 18, "ordinarily," should be --Ordinarily,--.

Column 12

Line 6, delete the phrase "in a range".

Line 6, delete the phrase "250,000 to about".

Line 7, insert --Daltons-- after "700,000".

Line 8-9, delete the phrase "in a range".

Line 9, delete the phrase "90,000 to about".

Line 9, insert --Daltons-- after "250,000".

Line 14, insert --Daltons-- after "50,000".

Column 13

Line 3, delete the phrase "in a range".

Line 3, delete the phrase "250,000 to about".

Line 4, insert --Daltons-- after "700,000".

Line 5, delete the phrase "in a range".

UNITED STATES PATENT AND TRADEMARK OFFICE
CERTIFICATE OF CORRECTION

PATENT NO. : 7,045,121 B2
APPLICATION NO. : 10/017817
DATED : May 16, 2006
INVENTOR(S) : Chang et al.

It is certified that error appears in the above-identified patent and that said Letters Patent is hereby corrected as shown below:

Column 13 (continued)

Line 6, delete the phrase "90,000 to about".

Line 6, insert --Daltons-- after "250,000".

Line 10, insert --Daltons-- after "50,000".

Signed and Sealed this

Eighteenth Day of March, 2008

JON W. DUDAS
*Director of the United States Patent and Trademark Office*